(12) United States Patent
Toyota et al.

(10) Patent No.: US 12,038,331 B2
(45) Date of Patent: Jul. 16, 2024

(54) WEARABLE DEVICE, AND BODY TEMPERATURE PRESENTATION SYSTEM

(71) Applicant: Nippon Telegraph and Telephone Corporation, Tokyo (JP)

(72) Inventors: Shin Toyota, Tokyo (JP); Kazuyoshi Ono, Tokyo (JP)

(73) Assignee: Nippon Telegraph and Telephone Corporation, Tokyo (JP)

( * ) Notice: Subject to any disclaimer, the term of this patent is extended or adjusted under 35 U.S.C. 154(b) by 120 days.

(21) Appl. No.: 17/794,042

(22) PCT Filed: Feb. 3, 2020

(86) PCT No.: PCT/JP2020/003885
§ 371 (c)(1),
(2) Date: Jul. 20, 2022

(87) PCT Pub. No.: WO2021/156904
PCT Pub. Date: Aug. 12, 2021

(65) Prior Publication Data
US 2023/0046325 A1    Feb. 16, 2023

(51) Int. Cl.
*G01J 5/48*  (2022.01)
*A61B 5/00*  (2006.01)
(Continued)

(52) U.S. Cl.
CPC .............. *G01J 5/485* (2022.01); *A61B 5/01* (2013.01); *A61B 5/6803* (2013.01);
(Continued)

(58) Field of Classification Search
CPC ......... G01J 5/485; H04N 23/71; H04N 23/45; H04N 5/33; A61B 5/01; A61B 5/6803;
(Continued)

(56) References Cited

U.S. PATENT DOCUMENTS

| 7,380,936 B2 * | 6/2008 | Howell ................ G02C 5/001 351/158 |
| 2004/0059212 A1 * | 3/2004 | Abreu .................. G02C 11/10 374/E13.002 |

(Continued)

FOREIGN PATENT DOCUMENTS

| CN | 107167932 A | 9/2017 |
| JP | 2006507855 A | 3/2006 |

(Continued)

OTHER PUBLICATIONS

Ohta et al., "Detection of Body Surface Temperature by Infrared Thermography for Prevention of Influenza Pandemic," NEC Technical Journal, vol. 62, No. 3, 2009, pp. 87-91. As described in the description.

*Primary Examiner* — Zaihan Jiang
(74) *Attorney, Agent, or Firm* — Slater Matsil, LLP

(57) ABSTRACT

A wearable device includes: a base to be worn on a head of a user; a first sensor that is provided to the base to be at a distance from a surface of the user's head and measures a first signal relating to a temperature of the surface of the user's head; an estimation circuit that estimates a body temperature of the user based on the first signal; and a display that presents the body temperature of the user estimated by the estimation circuit.

15 Claims, 10 Drawing Sheets

(51) Int. Cl.
  *A61B 5/01*    (2006.01)
  *G06F 3/16*    (2006.01)
  *H04N 5/225*   (2006.01)
  *H04N 5/235*   (2006.01)
  *H04N 5/33*    (2023.01)
  *H04N 23/45*   (2023.01)
  *H04N 23/71*   (2023.01)

(52) U.S. Cl.
  CPC .......... *A61B 5/7405* (2013.01); *A61B 5/7445* (2013.01); *G06F 3/16* (2013.01); *H04N 5/33* (2013.01); *H04N 23/45* (2023.01); *H04N 23/71* (2023.01); *A61B 2560/0247* (2013.01)

(58) Field of Classification Search
  CPC ................ A61B 5/7405; A61B 5/7445; A61B 2560/0247; G06F 3/16
  See application file for complete search history.

(56) References Cited

U.S. PATENT DOCUMENTS

| | | | |
|---|---|---|---|
| 2007/0109491 A1* | 5/2007 | Howell | A61B 5/02433 351/41 |
| 2015/0116650 A1* | 4/2015 | Li | G02C 7/101 351/47 |
| 2015/0279168 A1* | 10/2015 | Avrahami | G04G 21/00 340/539.11 |
| 2016/0198995 A1* | 7/2016 | Yeung | A61B 5/1118 600/595 |
| 2018/0026977 A1* | 1/2018 | Matsenko | H04L 12/2803 340/506 |
| 2021/0289283 A1* | 9/2021 | Cavarra | G06F 3/011 |

FOREIGN PATENT DOCUMENTS

| | | | |
|---|---|---|---|
| WO | WO-2018184072 | * | 4/2017 |
| WO | WO 2018184072 | * | 6/2018 |

* cited by examiner

WEARABLE DEVICE, AND BODY TEMPERATURE PRESENTATION SYSTEM

CROSS-REFERENCE TO RELATED APPLICATIONS

This application is a national phase entry of PCT Application No. PCT/JP2020/003885 filed on Feb. 3, 2020, which application is hereby incorporated herein by reference.

TECHNICAL FIELD

The present invention relates to a wearable device and a body temperature presentation system.

BACKGROUND

Conventionally, a body temperature measurement device has been known that captures a thermal image of a user by means of infrared thermography and estimates the body temperature, such as the deep body temperature, of the user from the obtained thermal image. Such a conventional body temperature measurement device is convenient because the body temperature of the user can be measured in a contactless manner.

Every object radiates energy at a certain wavelength by vibration or rotation of atoms and molecules as long as it is above absolute zero (0K: −273.15° C.). Infrared thermography involves receiving the energy radiated from an object and obtaining the temperature of the object based on the Stefan-Boltzmann law to visualize it as two-dimensional temperature distribution.

Making use of such characteristics, infrared thermography has been put into a wide range of applications such as electric and electronic fields as well as quality management of industrial products, plant maintenance, structural inspection, and security monitoring.

For example, Non-Patent Literature 1 discloses a technique of applying a body temperature measurement device using conventional infrared thermography to pandemic measures. More specifically, Non-Patent Literature 1 discloses a technique for preventing the spread of diseases by installing a body temperature measurement device using infrared thermography at an airport gate or the like to detect fever of a person due to diseases such as influenza.

Incidentally, against the background of population aging and increasing interest in health in recent years, there is a need for a technique of monitoring the physical conditions and health by using the body temperature and other biological information.

For example, in the case of measuring the body temperature of a user in a contactless manner by using conventional infrared thermography as a measure against heatstroke in a situation where the movement direction of the user is not fixed, such as when the user is exercising, the body temperature of the user may not be detected with a fixed-type body temperature measurement device, depending on the position where the user moves.

In addition, although there is also a conventional technique for monitoring the body temperature of an individual user by using a contact-type temperature sensor, the decreased breathability at the portion of contact between the user's body and the temperature sensor and the skin feeling of contact with the temperature sensor may not only cause psychological discomfort to the user but also skin rashes or the like for some people.

CITATION LIST

Non-Patent Literature

Non-Patent Literature 1: Jiro Ohta, Eri Hamada, "Detection of Body Surface Temperature by Infrared Thermography for Prevention of Influenza Pandemic", NEC Technical Journal Vol. 62, No. 3/2009, pp. 87-91.

SUMMARY

Technical Problem

Embodiments of the present invention have been made in order to solve the above-described problem, and it is an object of embodiments of the present invention to measure and present the body temperature of each user in a contactless manner.

Means for Solving the Problem

In order to solve the above-described problem, a wearable device according to the embodiments of present invention includes: a base to be worn on a head of a measurement subject; a first sensor that is provided to the base to be at a distance from a surface of the head of the measurement subject and measures a first signal relating to a temperature of the surface of the head of the measurement subject; an estimation circuit that estimates a body temperature of the measurement subject based on the first signal; and a presentation device that presents the body temperature of the measurement subject estimated by the estimation circuit.

In order to solve the above-described problem, a body temperature presentation system according to embodiments of the present invention includes: a wearable device including: a base to be worn on a head of a measurement subject; a first sensor that is provided to the base and measures a first signal relating to a temperature of the surface of the head of the measurement subject; and a second sensor that is provided to the base and measures a second signal indicating an intensity of ambient light at a position of the surface of the head where the first signal is measured; and a communication terminal device connected to the wearable device via a network, wherein at least one of the wearable device and the communication terminal device includes an estimation circuit that estimates a body temperature of the measurement subject by correcting the first signal based on the second signal, and the communication terminal device includes a presentation device that presents the body temperature estimated by the estimation circuit.

Effects of Embodiments of the Invention

According to embodiments of the present invention, since the first sensor that is provided to the base to be at a distance from the surface of the head of the measurement subject and measures the first signal relating to the temperature of the surface of the head of the measurement subject and the presentation device that presents the body temperature of the measurement subject estimated based on the first signal are provided, it is possible to measure and present the body temperature of each user in a contactless manner.

DETAILED DESCRIPTION OF ILLUSTRATIVE EMBODIMENTS

Preferred embodiments of the present invention will be described in detail below with reference to FIGS. 1 to 10.

First Embodiment

Figure 1:
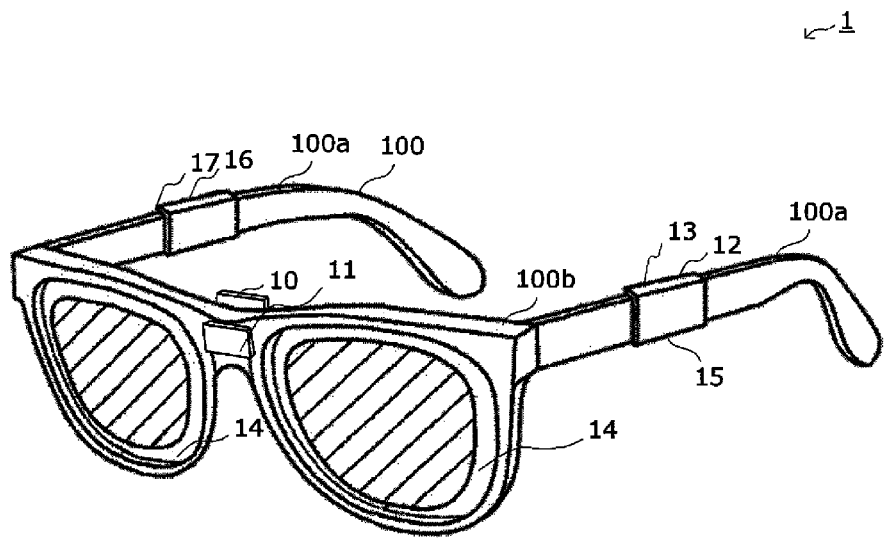
FIG. 1 is a diagram showing the external appearance of a wearable device according to a first embodiment of the present invention.

FIG. 1 is an example external view of a wearable device 1 according to a first embodiment of the present invention. Hereinafter, description will be made assuming that the "head" of a user includes his/her "face".

[General Configuration of Wearable Device]

As shown in FIG. 1, the wearable device 1 according to the first embodiment is realized by an eyeglass-type terminal such as smartglasses. The wearable device 1 is worn on the head of a user that is a subject on which to perform body temperature measurement. The wearable device 1 includes a base 100 having a frame structure including temples 100a and rims 100b and a display 14 supported by the base 100. In the present embodiment, a presentation device is realized by the eyeglass lens-type display 14.

The temples 100a are a left-and-right pair of parts formed to sandwich the sides of the user's head, as shown in FIG. 1. The temples 100a have a shape elongated along the sides of the head in the horizontal direction and has a thickness suitable to be worn by the user. The rear-side portions of the temples 100a contact the upper and rear portions of the user's ears and push the sides of the user's head to prevent the wearable device 1 from falling. In addition, the front-side portions of the temples 100a are connected to the rims 100b via hinges or the like. The rims 100b are formed along the shape of the eyeglass lens-type display 14.

Hereinafter, surfaces of the temples 100a and the rims 100b facing or contacting the user's face or head when the wearable device 1 is worn by the user may be referred to as face-side or inner-side surfaces, and surfaces of the temples 100a and the rims 100b on the outer side may be referred to as outer-side surfaces.

The rims 100b of the wearable device 1 are provided with a first sensor 10 that measures a first signal relating to the temperature of the surface of the user's head, for example, face. For example, as shown in FIG. 1, the first sensor 10 is arranged on the inner-side surface of the rims 100b when the wearable device 1 is worn on the user's head. Note that the first sensor 10 may be formed integrally with the rims 100b or may be detachably or non-detachably attached to the rims 100b.

Further, the rims 100b of the wearable device 1 are provided with a second sensor that measures a second signal indicating ambient light at the position of the surface of the user's body where the first signal is measured. For example, as shown in FIG. 1, the second sensor 11 is arranged on the outer-side surface of the rims 100b along the direction of the visual field from the inner-side surface of the rims 100b on which the first sensor 10 is provided when the wearable device 1 is worn on the user's head. The second sensor 11 may be formed integrally with the rims 100b or may be detachably or non-detachably attached to the rims 100b.

Inside the temples 100a of the wearable device 1 according to the present embodiment, an estimation circuit 12 that estimates the body temperature of the user by correcting the first signal by the second signal, a generation circuit 13 that generates image content indicating the body temperature estimated by the estimation circuit 12, a memory 15, a power supply 16, and a switch 17 are provided.

In the example shown in FIG. 1, a computational processing unit including the estimation circuit 12, the generation circuit 13, and the memory 15 is housed in a housing having a shape corresponding to the width (vertical length) and thickness of the temples 100a, and the housing is embedded in either the left or right temple 100a. In addition, the power supply 16 and the switch 17 are housed in a housing having a shape corresponding to the width and thickness of the temples 100a and embedded in the other temple 100a.

Lines (not shown) are provided inside the temples 100a and the rims 100b of the wearable device 1, and the first sensor 10, the second sensor 11, the estimation circuit 12, the generation circuit 13, the display 14, the memory 15, the power supply 16, and the switch 17 are electrically connected.

In the present embodiment, the eyeglass lens-type display 14 displays, visibly to the user, image content such as text data "36.5° C." indicating the body temperature of the user generated by the generation circuit 13.

[Components of Wearable Device]

Figure 2:
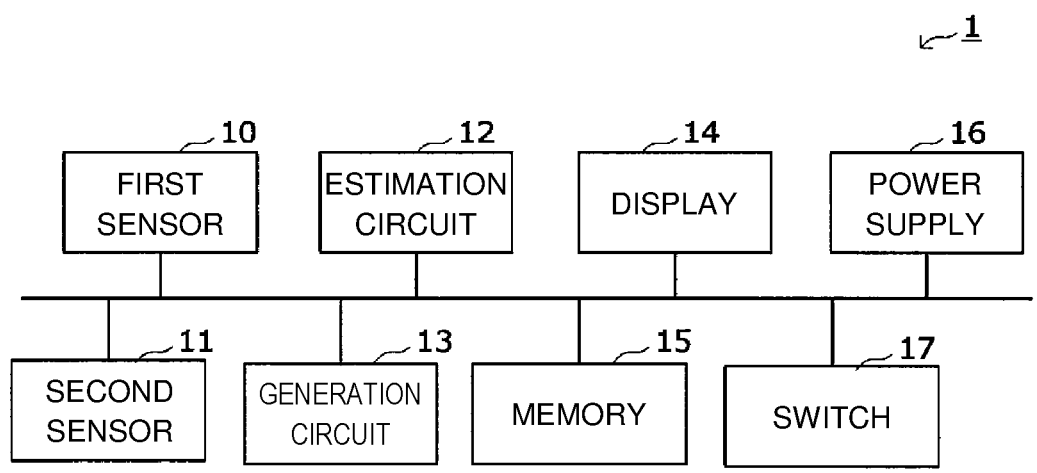
FIG. 2 is a block diagram showing the configuration of the wearable device according to the first embodiment of the present invention.

Next, components included in the wearable device 1 according to the present embodiment will be described in more detail with reference to FIGS. 2 and 3.

The first sensor 10 is constituted by a temperature sensor or the like and measures a first signal indicating the temperature of the surface of the user's face wearing the wearable device 1. The first sensor 10 is arranged on the inner-side surface of the rims 100b, and thus, when the user wears the wearable device 1, the first sensor 10 is always arranged at a position distanced from the user's face by a certain distance.

For example, an infrared temperature sensor that absorbs infrared light and converts it into an electric signal is used as the first sensor 10. In this case, as the first signal measured by the first sensor 10, an intensity of infrared light obtained by converting infrared radiation energy emitted from the surface of the user's face into an electric signal is acquired. The first sensor 10 further includes an amplification circuit, an AD conversion circuit, and the like (not shown). The first signal measured by the first sensor 10 is input to the estimation circuit 12.

In the example of FIG. 1, a single first sensor 10 is arranged on the inner side, that is, the user's face-side of the central portion of the rims 100*b* of the wearable device 1. However, there may be a plurality of first sensors 10 and, for example, the plurality of first sensors 10 may be arranged on the inner side of the left and right rims 100*b*.

Figure 3:
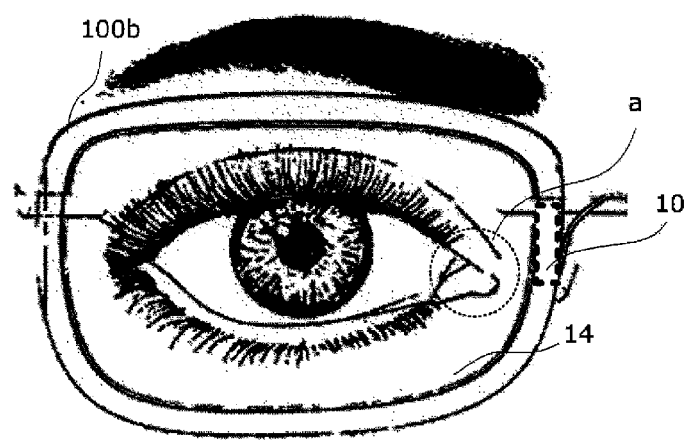
FIG. 3 is a diagram showing an example of body temperature measurement by the wearable device according to the first embodiment of the present invention.

For example, as shown in FIG. 3, the first sensor 10 is arranged on the inner-side surface of a rim 100*b* close to the inner corner of the user's eye on the wearable device 1. By arranging the first sensor 10 in no contact with the user's skin and at a position closer to the inner corner of the eye, the first signal indicating the temperature of a region "a" of the inner corner of the user's eye can be measured.

The portion of the inner corner of the eye in the region of one's face includes a pink-colored thin membrane referred to as a semilunar fold. The semilunar fold is not covered with skin and has blood vessels running through it, and thus is a portion that is most likely to reflect the internal body temperature at the center of the body when surface temperature distribution of the entire face is measured. Thus, the region "a" of the inner corner of the eye is used as a target region where the first signal indicating the temperature is to be measured by the first sensor 10.

The second sensor 11 is constituted by a light sensor provided with a photodiode and the like and measures the second signal indicating the intensity of ambient light at the position of the surface of the user's face where the first signal is measured by the first sensor 10. The second sensor 11 detects the intensity of the ambient light at the position where it is installed, and converts it into the second signal, which is an electric signal corresponding to the detected light intensity. The second sensor 11 further includes an amplification circuit, an AD conversion circuit, and the like (not shown). The second signal measured by the second sensor 11 is input to the estimation circuit 12.

The second sensor 11 measures the second signal indicating ambient light of the region "a" where the first signal is measured. In the example of FIG. 1, it is arranged at the central portion of the outer-side surface of the rims 100*b* such that the ambient light is not blocked when the user wears the wearable device 1.

The estimation circuit 12 estimates the body temperature of the user based on the first signal indicating the surface temperature of the face such as the temperature of the region "a" of the inner corner of the user's eye and the second signal indicating the intensity of ambient light. The first signal measured by the first sensor 10 constituted by the infrared temperature sensor is data indicating the surface temperature of the user's face as well as data affected by diffracted light and reflected light. Thus, the first signal is corrected by excluding the effects of light other than the infrared light emitted from the surface of the user's face included in the first signal by using the second signal, which indicates the intensity of ambient light measured by the second sensor 11, to estimate the body temperature of the user.

Here, if the first signal measured by the first sensor 10 is represented as E, E includes radiation energy $E_1$ emitted from the surface of the user's face, which is the measurement target, and radiation energy $E_2$ due to the ambient effects represented by the second signal ($E=E_1+E_2$). As is well known, the temperature, T, of the surface of the user's face, which is the measurement target, can be obtained if a spectral emissivity $\varepsilon_\lambda$ ($\varepsilon_\lambda<1$, because the skin is not black-body) and an ambient temperature Ta are known. As the spectral emissivity $\varepsilon_\lambda$ of the measurement-target surface, a value experimentally evaluated in advance or a value indicated in a literature or the like can be used.

As above, the estimation circuit 12 uses the known spectral emissivity $\varepsilon_\lambda$ to calculate the intensity of infrared light emitted from the surface of the user's face, which is obtained by excluding the effects of diffracted light and reflected light represented by the second signal from the first signal.

The estimation circuit 12 also estimates the body temperature of the user based on the corrected intensity of infrared light (first signal). For example, the estimation circuit 12 can estimate, as the body temperature, a value obtained by multiplying data of the corrected intensity of infrared light by moving average. Note that the estimation circuit 12 outputs the estimated value of the body temperature of the user at a constant period.

The generation circuit 13 generates image content indicating the body temperature of the user estimated by the estimation circuit 12. For example, the generation circuit 13 generates set image content such as a graphic content indicating a numerical value or temperature distribution indicating the body temperature. The generation circuit 13 can generate the image content in accordance with the period at which the estimation circuit 12 outputs the estimated value.

The generation circuit 13 may also generate the image content when the body temperature of the user estimated by the estimation circuit 12 becomes above or below a preset value. For example, an alarm image may be generated when a certain rise or decrease in the body temperature is detected.

The display 14 is constituted by a transparent display arranged at the positions of the lenses of the eyeglasses, and displays, visibly to the user, the image content indicating the body temperature of the user generated by the generation circuit 13. In addition to the body temperature of the user generated by the generation circuit 13, the display 14 can also present, visibly to the user, an environmental temperature, humidity, or the like measured by an environmental temperature sensor or the like (not shown). For example, the display 14 can update, at a constant period, and display the image content indicating the body temperature of the user generated by the generation circuit 13.

The memory 15 is constituted by a semiconductor memory or the like, and memorizes sensor data measured by the first sensor 10 and the second sensor 11, the body temperature of the user estimated by the estimation circuit 12, and the like. The memory 15 also stores an estimation program used by the estimation circuit 12 and the generation circuit 13, a program for generating the image content, and the like. The memory 15 also memorizes calibration data for the first sensor 10 and the second sensor 11. Further, the memory 15 has a region for backing up various pieces of data.

Note that the estimation circuit 12, the generation circuit 13, and the memory 15 can be realized by a computer constituted by a processor and a primary storage device. In addition, the estimation circuit 12 and the generation circuit 13 can each be realized by an FPGA, an ASIC, or the like.

The power supply 16 is constituted by a battery such as a lithium-ion secondary battery, and supplies electric power to the wearable device 1 including the estimation circuit 12 and the generation circuit 13.

The switch 17 is constituted by a switch circuit for controlling the power supply 16 to be turned on/off. A physical button, touch switch, or the like as the switch 17 is provided at a position where it can be easily operated when the user wears the wearable device 1, for example, on the outer side of the temple 100a, and the power supply 16 is turned on/off in response to a push operation or touch operation by the user.

The eyeglass-type wearable device 1 having the above-described configuration is worn on the user's head, and, for example, the power supply 16 is turned on when a touch operation on the switch 17 is performed by a user's finger or the like. The power supply 16 is turned on, electric power is supplied to the wearable device 1, and the first sensor 10 measures the first signal indicating the temperature of the surface of the user's head, for example, of the region "a" of the inner corner of the eye. In addition, the second sensor 11 measures the second signal indicating the intensity of ambient light in the region "a".

The first signal and the second signal measured are input to the estimation circuit 12, the first signal is corrected by the second signal, and the body temperature of the user is estimated from a value from which the effects of external disturbance light are excluded. The estimated value of the body temperature of the user is input to the generation circuit 13, and image content in a preset form is generated. For example, a text image of the estimated value of the body temperature or the like is generated and presented on the eyeglass lens-type display 14. The user wearing the wearable device 1 can recognize the body temperature displayed on the display 14 by means of visual information.

As described above, according to the first embodiment, the body temperature of each user can be measured and presented in a contactless manner by the eyeglass-type wearable device 1 including the first sensor 10 and the second sensor 11.

In addition, according to the first embodiment, image content indicating the body temperature of the user is presented, visibly to the user, on the eyeglass lens-type display 14 at a constant period, and thus it is possible to make notification of a rise or decrease in the body temperature of the user.

In addition, according to the first embodiment, the wearable device 1 is realized by an eyeglass-type terminal device such as smartglasses. Thus, the user can easily recognize his/her body temperature or a change in his/her body temperature from information displayed on the display 14 only by wearing the wearable device 1 on the head and operating the power supply button.

Note that, in the described embodiment, the case where a single first sensor 10 is provided to the wearable device 1 has been described. However, as mentioned above, there may be a plurality of first sensors 10. If a plurality of first sensors 10 are used, the estimation circuit 12 can perform the correction process for each first signal indicating a temperature measured by each of the first sensors 10 to estimate the body temperature. The estimation circuit 12 can estimate, as the body temperature, a value obtained by averaging a plurality of first signals corrected by using the second signal.

It is also possible to estimate, based on first signals measured by a plurality of first sensors 10 arranged at different positions on the base 100, the body temperature by rendering temperatures indicated by the first signals corrected by the second signal into temperature distribution with a certain number of pixels.

In addition, although the case where the estimation circuit 12 performs the correction process and the body temperature estimation process is illustrated in the described embodiment, it is also possible to realize the correction process and the body temperature estimation process by another circuit.

Second Embodiment

Next, a second embodiment of the present invention will be described. Note that, in the following description, the same components as in the first embodiment described above are given the same reference characters, and their descriptions will be omitted.

In the first embodiment, the case where the wearable device 1 is realized by an eyeglass-type terminal device such as smartglasses has been described. In contrast, a wearable device 1A according to the second embodiment further includes an attachment member 101A for detachable fixation to common eyeglasses G worn by the user. The wearable device 1A is attached to the eyeglasses G with the attachment member 101A and worn by the user. In the following, different components than in the first embodiment will be mainly described.

Figure 4:
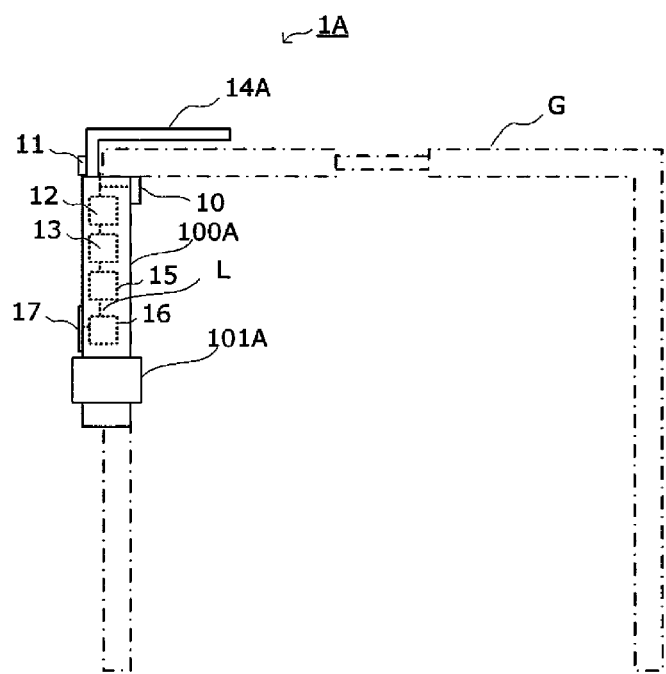
FIG. 4 is a schematic plan view of a wearable device according to a second embodiment of the present invention.

FIG. 4 is a schematic plan view of the wearable device 1A according to the present embodiment. Long dashed short dashed lines shown in FIG. 4 indicate the common eyeglasses G worn by the user. The eyeglasses G include frame structures worn on the user's head such as eyewear such as sunglasses, prescription eyeglasses, and goggles, and a headset.

The wearable device 1A includes a base 100A whose outer shape is a rectangular parallelepiped having a size corresponding to the width and length of the temples of the eyeglasses G, for example. An estimation circuit 12, a generation circuit 13, a memory 15, and a power supply 16 are housed inside the base 100A. In the following description, regarding the base 100A having a rectangular parallelepiped outer shape, a surface shown in the plan view of FIG. 4 is referred to as an upper surface of the base 100A, a surface opposite to the upper surface in a direction perpendicular to the paper plane is referred to as a bottom surface, and other surfaces are referred to as side surfaces.

For example, as shown in FIG. 4, the longitudinal length of the base 100A in the plan view is shorter than the longitudinal length of the temples of the eyeglasses G, and the lateral length of the base 100A is formed to be slightly larger than the thickness of the temples of the eyeglasses G. In addition, the dimension of the base 100A in a direction perpendicular to the paper plane in FIG. 4 is formed to be substantially equal to the width of the temples of the eyeglasses G, for example. Resin, an alloy, wood, or the like can be used for the material of the base 100A.

For example, the base 100A has a structure attachable to one of the left and right temples of the common eyeglasses G as shown in FIG. 4. In the example of FIG. 4, an attachment member 101A for detachably fixing the base 100A and the temple of the eyeglasses G is provided. The attachment member 101A may be formed of the same material as the base 100A, or may be formed of a material having a higher strength than the material used for the base 100A.

Note that the attachment member 101A is only required to be capable of attaching and fixing the wearable device 1A at a predetermined position of the eyeglasses G and, for example, the attachment member 101A may be formed integrally with the base 100A. For example, the attachment member 101A may be formed with a clip sandwiching one of the left and right temples of the eyeglasses G along the longitudinal direction shown in FIG. 4 on the bottom surface of the base 100A.

For example, the wearable device 1A can also be attached to the eyeglasses G by hanging the attachment member 101A formed on the base 100A on the temple of the eyeglasses G from the upper side (in the up-down directions with respect to the ground). In addition, as shown in FIG. 4, setting the attachment position of the base 100A closer to the lens of the eyeglasses G can prevent the user from perceiving the unevenness of the base 100A.

For example, the user can start measurement of the body temperature by attaching and fixing the wearable device 1A to the eyeglasses G that he/she usually uses and performing a touch operation on a switch 17.

A first sensor 10 is arranged on a side surface of the base 100A on the inner side of the eyeglasses G, that is, on the user's face-side when the user wears the eyeglasses G and at a position to be distanced from the user's face and the sides of the user's head. The first sensor 10 measures a first signal indicating the temperature of the surface of the user's face, for example, the temperature of a region "a" of the inner corner of the eye.

A second sensor 11 is provided at a position close to the position of the first sensor 10 on the outer side of the eyeglasses G, that is, on a side surface of the base 100A facing outward when the user wears the eyeglasses G. The second sensor 11 measures a second signal indicating the intensity of ambient light on the surface of the user's face where the first signal is measured, for example, in the region "a".

A display 14A is provided on a side surface of the base 100A in front of where the first sensor 10 and the second sensor 11 are arranged. In the example of FIG. 4, the display 14A is provided in alignment with the position of the left lens of the eyeglasses G. As shown in FIG. 4, when the eyeglasses G to which the wearable device 1A is attached is worn by the user, the body temperature displayed on the display 14A via the lens of the eyeglasses G can be displayed visibly to the user.

The switch 17 is arranged on a side surface of the base 100A that is on the outer side when the user wears the eyeglasses G.

The first sensor 10, the second sensor 11, the estimation circuit 12, the generation circuit 13, the display 14, the memory 15, the power supply 16, and the switch 17 are electrically connected via a line L. Note that their configurations and functions are similar to those in the first embodiment.

As described above, in the second embodiment, since the wearable device 1A is detachably fixed to the common eyeglasses G, convenience is improved, and it is possible to measure and present the body temperature of each user in a contactless manner.

Note that, although the case where the base 100A of the wearable device 1A has a rectangular parallelepiped outer shape has been illustrated in the described embodiment, the shape of the base 100A may be any shape as long as the estimation circuit 12, the generation circuit 13, the memory 15, the power supply 16, and the switch 17 can be housed inside it. For example, the base 100A having a cylindroid outer shape may also be used.

Third Embodiment

Next, a third embodiment of the present invention will be described. Note that, in the following description, the same components as in the first and second embodiments described above are given the same reference characters, and their descriptions will be omitted.

Regarding the wearable devices 1 and 1A according to the first and second embodiments, the case where the measurement of the temperature and ambient light, estimation process, and presentation process are performed by one device has been described. In contrast, the third embodiment is an invention relating to a body temperature presentation system including a wearable device 1B and a communication terminal device 200. The body temperature presentation system has a configuration in which the functions of the wearable devices 1 and 1A according to the first and second embodiments are distributed.

Figure 5:
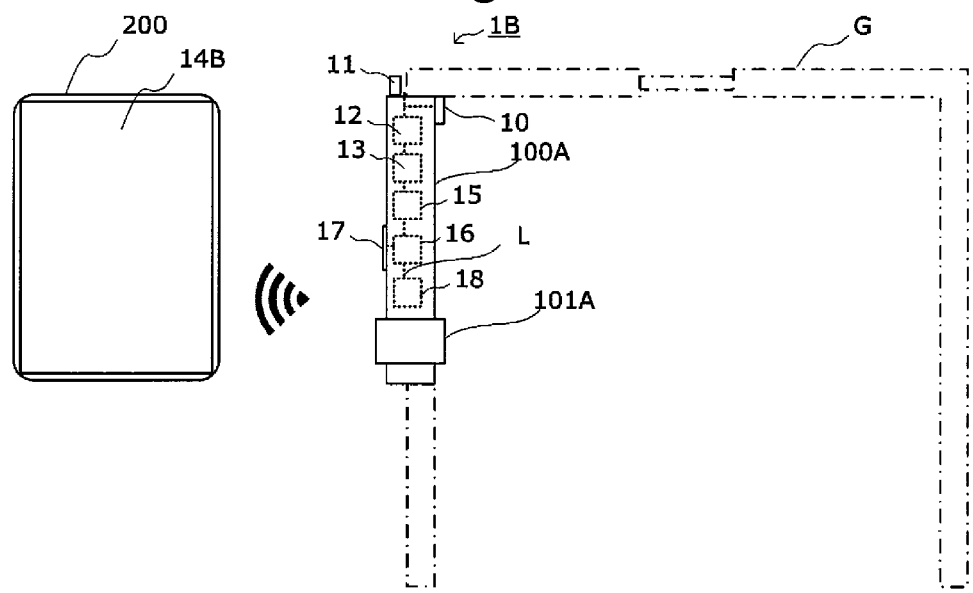
FIG. 5 is a block diagram showing the configuration of a body temperature presentation system according to a third embodiment of the present invention.

FIG. 5 is a block diagram showing an example configuration of the body temperature presentation system according to the third embodiment. As shown in FIG. 5, the body temperature presentation system includes the wearable device 1B and the communication terminal device 200. In the example shown in FIG. 5, a display 14B is installed in the communication terminal device 200.

[Configuration of Wearable Device]

The wearable device 1B includes a base 100A having a rectangular parallelepiped outer shape, a first sensor 10 arranged on a face-side side surface of the base 100A, a second sensor 11 arranged on an outer-side side surface of the base 100A, a switch 17, and an attachment member 101A. In addition, an estimation circuit 12, a generation circuit 13, a memory 15, a power supply 16, and a communication I/F 18 are housed inside the base 100A having a rectangular parallelepiped outer shape and are electrically connected via a line L.

The wearable device 1B according to the present embodiment is different than in the second embodiment in that it does not include the display 14B that indicates the body temperature of the user generated by the generation circuit 13. Note that the functions and configurations of the first sensor 10, the second sensor 11, the estimation circuit 12, the generation circuit 13, the memory 15, the power supply 16, and the switch 17 are similar to those in the first and second embodiments.

The communication I/F 18 is an interface circuit for performing communication with the communication terminal device 200 via a network. As the communication I/F 18, for example, a communication control circuit and an antenna compatible with wireless data communication standards such as 3G, 4G, 5G, wireless LAN, Bluetooth (R), and Bluetooth Low Energy are used.

In the present embodiment, when image content such as text information indicating the body temperature of the user is generated by the generation circuit 13, data of the image content indicating the body temperature is sent from the communication I/F 18 to the communication terminal device 200 via the network.

[Configuration of Communication Terminal Device]

Next, the configuration of the communication terminal device 200 will be described in in more detail.

The communication terminal device 200 is a terminal device having a communication function and a presentation device, such as a smartphone, tablet terminal, or notebook PC. For example, the communication terminal device 200 is used by the user wearing the wearable device 1B. In addition, in the example configuration of the body temperature presentation system shown in FIG. 5, the display 14B is provided to the communication terminal device 200.

When receiving the data of the image content indicating the body temperature of the user from the wearable device 1B, the communication terminal device 200 causes the display 14B to display the received image content. For example, the display 14B is realized by a liquid crystal display or the like.

Next, an example computer configuration for realizing the communication terminal device 200 will be described with reference to the block diagram of FIG. 6.

Figure 6:
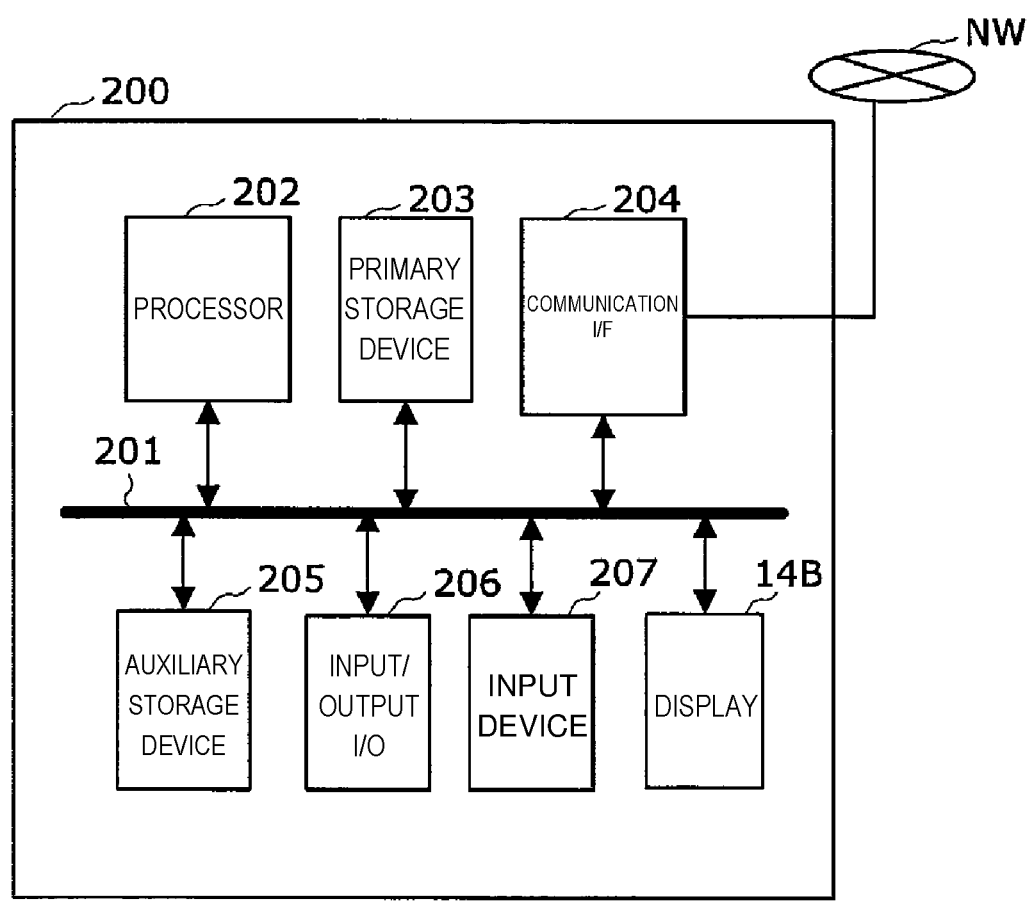
FIG. 6 is a block diagram showing an example of hardware configuration realizing a communication terminal device according to the third embodiment of the present invention.

As shown in FIG. 6, for example, the communication terminal device 200 can be realized by a computer including a processor 202, a primary storage device 203, a communication I/F 204, an auxiliary storage device 205, and an input/output I/O 206 connected via a bus 201 and programs for controlling these hardware resources. In the communication terminal device 200, for example, an input device 207 and the display 14B are each connected via the bus 201.

Programs for the processor 202 performing various control and computation operations are stored in advance in the primary storage device 203.

The communication I/F 204 is an interface circuit for performing communication with various pieces of external electronic equipment such as the wearable device 1B via a network NW.

As the communication I/F 204, for example, a communication control circuit and an antenna compatible with wireless data communication standards such as 3G, 4G, 5G, wireless LAN, Bluetooth (R), and Bluetooth Low Energy are used.

The auxiliary storage device 205 is constituted by a readable/writable storage medium and a driving device for reading/writing various pieces of information such as programs and data from/to the storage medium. A semiconductor memory such as a hard disk or a flash memory as a storage medium can be used for the auxiliary storage device 205.

The input/output I/O 206 is constituted by an I/O terminal that inputs a signal from external equipment and outputs a signal to external equipment.

The input device 207 is constituted by a keyboard, a touch panel, or the like, and accepts an external operation input and generates a signal corresponding to the operation input.

Note that, regarding the body temperature presentation system shown in FIG. 5, the case where the communication terminal device 200 includes the display 14B that presents the body temperature of the user has been illustrated. However, as long as the wearable device 1B includes the first sensor 10 and the second sensor 11, other components can be included in the communication terminal device 200.

In addition, as is similar to the first and second embodiments, it is also possible that the wearable device 1B includes the eyeglass lens-type display 14B and the communication terminal device 200 includes the estimation circuit 12 and the generation circuit 13 that generates image content.

In addition, a plurality of relay terminal devices may be provided between the wearable device 1B and the communication terminal device 200 so that the wearable device 1B and the communication terminal device 200 perform data exchange via each relay terminal device. Routers and IoT gateways can be used as the relay terminal devices.

For example, it is assumed that a configuration is used in which computational processes including the estimation circuit 12 and the generation circuit 13 are performed by the communication terminal device 200 realized by a server, a cloud server, or the like. In this case, for example, the communication terminal device 200 can obtain analysis data such as an average or distribution of the body temperatures of a plurality of users based on temperature-related data from the wearable device 1B worn by each of the plurality of users, and present the analysis data to the communication terminal device 200 and the display 14B of the wearable device 1B. In addition, for example, it is possible that positional information of relay terminal devices is regarded as positional information of users, and information of a user whose body temperature is higher than a set value among the plurality of users is displayed on a display screen of the communication terminal device 200 or notified to a particular terminal device.

As described above, since the body temperature presentation system according to the third embodiment includes the wearable device 1B including at least the first sensor 10 and the second sensor 11 and the communication terminal device 200 in communication with the wearable device 1B, analysis of the body temperature of the user measured in a contactless manner can be made easier. In particular, it is effective in the case of analyzing the body temperatures of a plurality of users, for example.

In addition, with the body temperature presentation system according to the third embodiment, by distributing computational processes including the estimation circuit 12 and the generation circuit 13 to the communication terminal device 200 on the network, computational load can be reduced.

Fourth Embodiment

Next, a fourth embodiment of the present invention will be described. Note that, in the following description, the same components as in the first to third embodiments described above are given the same reference characters, and their descriptions will be omitted.

The first to third embodiments have been described with reference to the case where the first signal relating to the temperature of the surface of the user's face and the second signal indicating the intensity of ambient light are measured by the first sensor 10 and the second sensor 11, respectively, to estimate and present the body temperature of the user. In contrast, a wearable device 1C according to a fourth embodiment further includes a camera 19 that acquires a thermal image of the visual field of the user.

Figure 7:
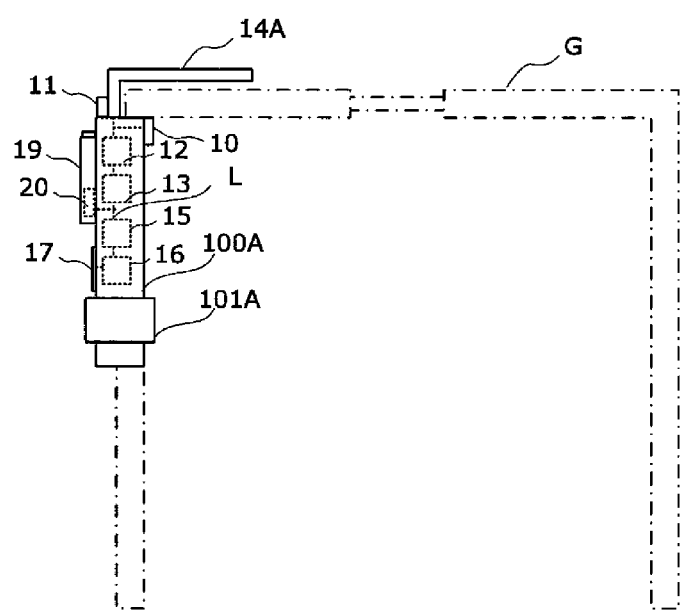
FIG. 7 is a schematic plan view of a wearable device according to a fourth embodiment of the present invention.

As shown in FIG. 7, the wearable device 1C according to the present embodiment further includes the camera 19 in the configuration described in the second embodiment.

For example, the camera 19 is arranged on an outer-side side surface of the base 100A and captures an image of the visual field of the user. For example, the camera 19 is constituted by an infrared camera or the like and acquires a thermal image of the visual field of the user. In addition, the camera 19 can further include a visible light camera and not only acquire a thermal image but also a visible light image of the visual field of the user.

Figure 8:
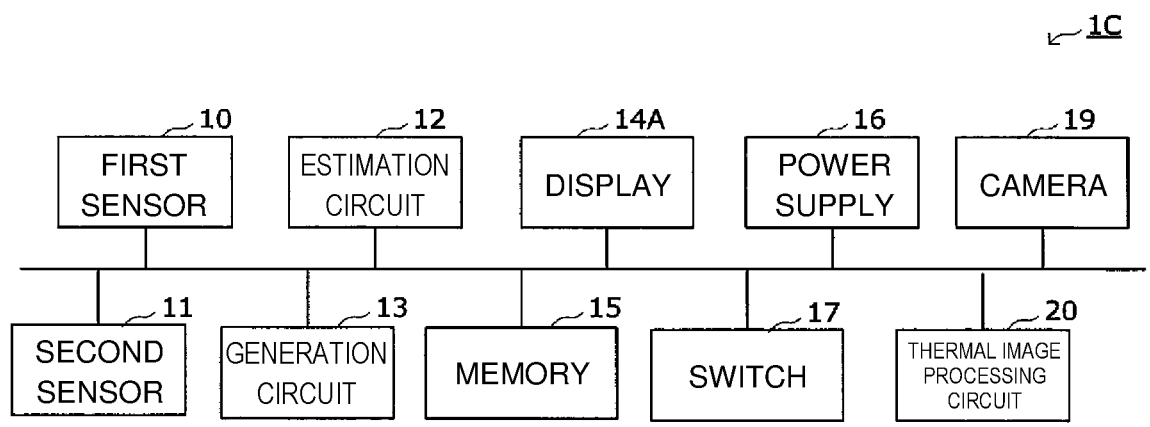
FIG. 8 is a block diagram showing the configuration of the wearable device according to the fourth embodiment of the present invention.

FIG. 8 is a block diagram showing the configuration of the wearable device 1C according to the present embodiment. The wearable device 1C includes a first sensor 10, a second sensor 11, an estimation circuit 12, a generation circuit 13, a display 14, a memory 15, a power supply 16, a switch 17, a camera 19, and a thermal image processing circuit 20. The components other than the camera 19 and the thermal image processing circuit 20 are similar to those in the first to third embodiments.

The camera 19 starts capturing an image when the power supply 16 is turned on in response to a push or touch operation on the switch 17 by the user. The image acquired by the camera 19 is input to the thermal image processing circuit 20.

The thermal image processing circuit 20 generates a thermal image indicating temperature distribution of the image captured by the camera 19. For example, the thermal image processing circuit 20 can generate an image in which thermal distribution is represented by gradation of colors like thermography. The thermal image processing circuit 20 can provide the thermal distribution image with 3D-space information such as clearer edges by processing the thermal image by using the visible light image captured by the camera 19. The thermal image output from the thermal image processing circuit 20 is displayed on the display 14A.

The thermal image processing circuit 20 can also generate a thermal image such that only preset temperature distribution is output to the display 14A. For example, it can generate an image such that cool locations, hot locations, and the like in the visual field of the user are presented visibly to the user. In addition, the image generated by the thermal image processing circuit 20 is not limited to the gradation image like thermography and can also be generated as data displayed by superimposing numerical values of information indicating thermal distribution on the visible light image, for example.

Figure 9:
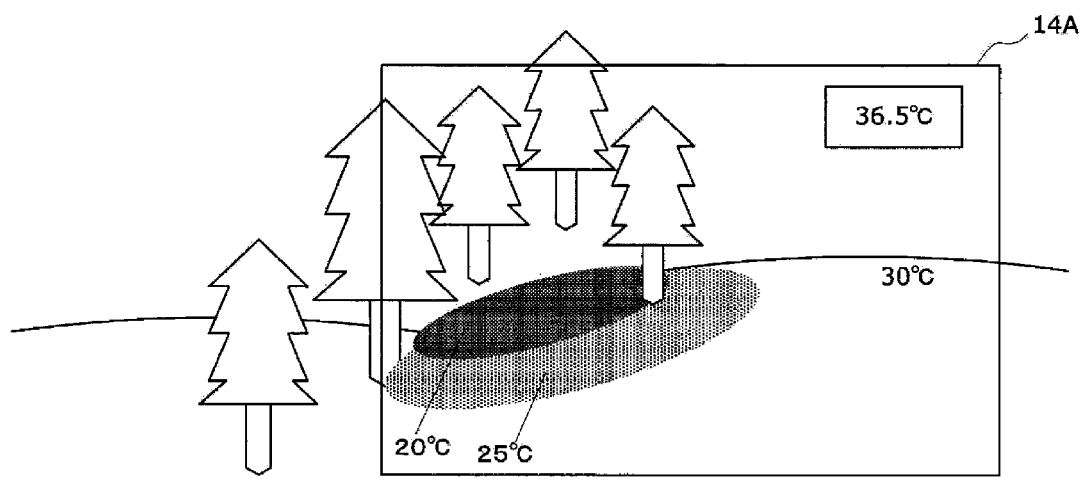
FIG. 9 is a diagram for illustrating an example of presentation by the wearable device according to the fourth embodiment of the present invention.

FIG. 9 is a schematic diagram showing an example of the thermal image and the body temperature of the user displayed on the display 14A. The body temperature of the user "36.5° C." is displayed as text data on the upper left of the display 14A.

In addition, regions "20° C.", "25° C.", and "30° C." indicating the thermal distribution of the visual field of the user generated by the thermal image processing circuit 20 are shown on the display 14A.

As shown in FIG. 9, information indicating the body temperature of the user and the thermal distribution in the visual field of the user is presented visibly to the user on the display 14A.

As described above, the wearable device 1B according to the fourth embodiment presents, visibly to the user, information indicating the measured body temperature of the user and the thermal distribution of the visual field of the user on the display 14A, and thus can easily guide the user to a cool location, a warm location, or the like.

For example, when the body temperature of the user presented on the display 14A is relatively high, the user can temporarily move to a cool location indicated in the thermal distribution presented on the display 14A, which enables application for prevention of heatstroke for the user by using the wearable device 1B.

Fifth Embodiment

Next, a fifth embodiment of the present invention will be described. Note that, in the following description, the same components as in the first to fourth embodiments described above are given the same reference characters, and their descriptions will be omitted.

In the first to fourth embodiments, the body temperature of the user is presented as visual information. In contrast, in the fifth embodiment, the body temperature of the user is presented by means of sound.

Figure 10:
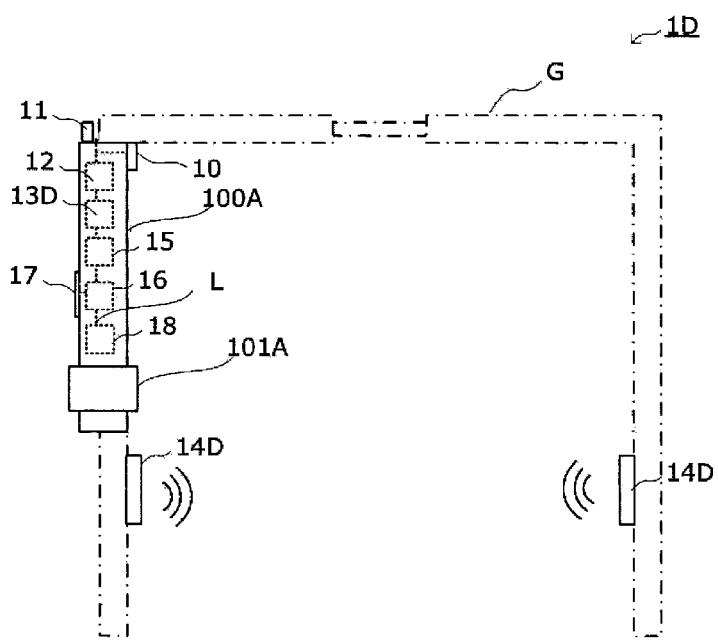
FIG. 10 is a schematic plan view showing the configuration of a wearable device according to a fifth embodiment of the present invention.

FIG. 10 is a schematic plan view showing an example configuration of a wearable device 1D according to the present embodiment. As shown in FIG. 10, for example, the wearable device 1D includes a base 100A having a rectangular parallelepiped outer shape and an attachment member 101A provided to the base 100A and fixed to eyeglasses G.

A first sensor 10 that measures a first signal indicating the temperature of the surface of the user's face, for example, of a region "a" of the inner corner of the eye is arranged on a face-side side surface of the base 100A. In addition, a second sensor 11 that measures a second signal indicating the intensity of ambient light in the region "a" is arranged on an outer-side side surface of the base 100A.

An estimation circuit 12, a generation circuit 13, a memory 15, and a power supply 16 are housed in the base 100A. In addition, a switch 17 is disposed on an outer-side side surface of the base 100A.

A line L is disposed inside the base 100A, and the estimation circuit 12, the generation circuit 13D, the memory 15, the power supply 16, the switch 17, and the communication I/F 18 are electrically connected by the line L.

The generation circuit 13D generates a sound audible to the user and indicating the body temperature of the user estimated by the estimation circuit 12. For example, the generation circuit 13D can generate a speech sound, alert sound, vibration, or the like indicating the body temperature.

The wearable device 1D includes a speaker 14D as a presentation device. For example, as shown in FIG. 10, a left-and-right pair of speakers 14D can be used. The speakers 14D output sound data such as speech sound indicating the body temperature generated by the generation circuit 13D.

For example, a bone conduction speaker can be used as the speaker 14D so that it can be attached to a temple of the eyeglasses G. For example, when the user wears the eyeglasses G to which the wearable device 1D is attached, the speakers 14D contact the sides of the user's head, the user's ears, and the like. The speakers 14D, the sound indicating the body temperature generated by the generation circuit 13D is transmitted through the temples of the eyeglasses G and output from the speakers 14D.

Alternatively, a wireless earphone can be used as the speaker 14D. In this case, for example, the communication I/F 18 housed in the base 100A and a communication I/F integrated in the speaker 14D perform short-range radio communication to send/receive sound data such as speech sound.

As described above, according to the fifth embodiment, the wearable device 1D presents information indicating the measured body temperature of the user by means of sound, and thus, the body temperature of each user measured in a contactless manner can be presented to the user even when the user has a visual disability or does not desire information such as the body temperature to be presented visibly to the outside, for example.

Although the embodiments of the wearable device and the body temperature presentation system of the present invention have been described above, the present invention is not limited to the described embodiments, and it is possible to make various modifications that can be conceived by those skilled in the art within the scope of the invention defined in the claims.

For example, the first to fifth embodiments described can be combined with each other. For example, it is also possible to output a sound such as an alert sound from the speaker 14D in addition to displaying the body temperature of the user on the display 14 as described in the first to fourth embodiments.

REFERENCE SIGNS LIST

1 Wearable device
10 First sensor
11 Second sensor
12 Estimation circuit
13 Generation circuit
14 Display 15 Memory
16 Power supply
17 Switch
100 Base
100a Temple
100b Rim.

The invention claimed is:

1. A wearable device comprising:
a base configured to be worn by a measurement subject;
a first sensor on the base and configured to measure a first signal corresponding to a temperature of a surface of the measurement subject;
an estimation circuit configured to estimate a body temperature of the measurement subject based on the first signal;
a presentation device configured to present the body temperature of the measurement subject estimated by the estimation circuit; and
a second sensor on the base and configured to measure a second signal indicating an intensity of ambient light at a position where the first signal is measured, wherein the estimation circuit is configured to correct the first signal based on the second signal and estimate the body temperature of the measurement subject based on the first signal that has been corrected based on the second signal.

2. The wearable device according to claim 1, further comprising:
a generation circuit configured to generate image content indicating the body temperature estimated by the estimation circuit,
wherein the presentation device includes a display supported by the base, and
wherein the display is configured to display, visibly to the measurement subject, the image content generated by the generation circuit.

3. The wearable device according to claim 2, further comprising:
a camera on the base and configured to acquire a thermal image of a visual field of the measurement subject,
wherein the display is configured to display, visibly to the measurement subject, the image content generated by the generation circuit and the thermal image acquired by the camera.

4. The wearable device according to claim 1, wherein:
the presentation device includes a speaker configured to output a sound indicating the body temperature.

5. The wearable device according to claim 1, wherein:
the first signal includes a signal indicating a temperature of a predetermined region on a face of the measurement subject.

6. The wearable device according to claim 1, further comprising:
an attachment member on the base or the presentation device, the attachment member detachably fixing the base to eyeglasses to be worn by the measurement subject,
wherein the presentation device is arranged in alignment with positions of lenses of the eyeglasses.

7. The wearable device according to claim 1, wherein a first sensor is configured to measure the first signal in a contactless manner with respect to the measurement subject.

8. A body temperature presentation system comprising:
a wearable device, and
a communication terminal device connected to the wearable device via a network,
wherein the wearable device comprises:
a base configured to be worn by a measurement subject;
a first sensor on the base and configured to measure a first signal corresponding to a temperature of a surface of the measurement subject; and
a second sensor on the base and configured to measure a second signal indicating an intensity of ambient light at a position where the first signal is measured; and
wherein
the wearable device or the communication terminal device includes an estimation circuit configured to estimate a body temperature of the measurement subject by correcting the first signal based on the second signal; and
the communication terminal device includes a presentation device configured to present the body temperature estimated by the estimation circuit.

9. The body temperature presentation system according to claim 8, wherein:
the first signal includes a signal indicating a temperature of a predetermined region on a face of the measurement subject.

10. The body temperature presentation system according to claim 8, further comprising:
an attachment member on the base, the attachment member detachably fixing the base to eyeglasses to be worn by the measurement subject.

11. The body temperature presentation system according to claim 8, wherein a first sensor is configured to measure the first signal in a contactless manner with respect to the measurement subject.

12. A method of operating a wearable device, the method comprising:
wearing, by a measurement subject, a base of the wearable device;
measuring, by a first sensor on the base, a first signal corresponding to a temperature of a surface of the measurement subject;
measuring, by a second sensor on the base, a second signal indicating an intensity of ambient light at a position where the first signal is measured;
correcting the first signal based on the second signal
estimating, by an estimation circuit of the wearable device, a body temperature of the measurement subject based on the first signal that has been corrected based on the second signal; and
presenting, by a presentation device of the wearable device, the body temperature of the measurement subject estimated by the estimation circuit.

13. The method of operating the wearable device according to claim 12, wherein measuring the first signal comprises measuring the first signal in a contactless manner with respect to the measurement subject.

14. The method of operating the wearable device according to claim 12, further comprising detachably fixing the base to eyeglasses to be worn by the measurement subject.

15. The method of operating the wearable device according to claim 12, further comprising detachably fixing the presentation device to eyeglasses to be worn by the measurement subject wherein the presentation device is arranged in alignment with positions of lenses of the eyeglasses.

* * * * *